(12) United States Patent
Hettrick (10) Patent No.: US 6,887,207 B2
(45) Date of Patent: May 3, 2005

(54) METHODS AND APPARATUS FOR ESTIMATION OF VENTRICULAR AFTERLOAD BASED ON VENTRICULAR PRESSURE MEASUREMENTS

(75) Inventor: Douglas A. Hettrick, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 204 days.

(21) Appl. No.: 10/376,064

(22) Filed: Feb. 26, 2003

(65) Prior Publication Data

US 2004/0167410 A1 Aug. 26, 2004

(51) Int. Cl.$^7$ .............................. A61B 5/02
(52) U.S. Cl. ............... 600/485; 600/481; 600/508; 607/17
(58) Field of Search .................. 600/481, 485, 600/486, 490, 508; 607/6, 17, 18, 23

(56) References Cited

U.S. PATENT DOCUMENTS

| | | | |
|---|---|---|---|
| 4,429,701 A | 2/1984 | Goor et al. | 128/713 |
| 4,664,125 A | * 5/1987 | Pinto | 600/485 |
| 5,368,040 A | 11/1994 | Carney | |
| 5,417,717 A | 5/1995 | Salo et al. | |
| 5,564,434 A | 10/1996 | Halperin et al. | |
| 5,626,623 A | 5/1997 | Kieval et al. | |

(Continued)

OTHER PUBLICATIONS

Kelly et al., "Effective Arterial Elastance as an Index of Arterial Vascular Load in Humans," *Circulation*, vol. 86, pp. 513–521 (1992).

Maughan et al., "Effect of Arterial Impedance Changes on the End–Systolic Pressure–Volume Relation," *Circulation Research*, vol. 54, p. 595–602 (1984).

(Continued)

*Primary Examiner*—Max F. Hindenburg
*Assistant Examiner*—Patricia Mallari
(74) *Attorney, Agent, or Firm*—Michael C. Soldner; Girma Wolde-Michael (57) ABSTRACT

A method and system incorporated into an IMD that detects changes in ventricular afterload using the morphology of a ventricular blood pressure wave. A peak positive pressure value $P_b$, peak positive and peak negative derivative pressures $dP/dt_{PP}$ and $dP/dt_{NP}$, and a decreasing pressure $P_c$ are determined. The sample times $t_b$, at $P_b$, $t_a$ at $dP/dt_{PP}$ and $t_c$ at $dP/dt_{NP}$ are determined. An index $\alpha$ of the relative timing of peak positive pressure $P_b$ in the blood ejection phase is calculated from, $\alpha=(t_b-t_a)/(t_c-t_a)$, the severity of ventricular afterload is proportional to the value $\alpha$ in the range between 0 and 1. The slope of the early ejection pressure in the blood ejection phase is calculated from $\beta=(P_c-P_b)/(t_c-t_b)$, wherein the severity of ventricular afterload is proportional to the magnitude of the index $\beta$.

43 Claims, 6 Drawing Sheets

U.S. PATENT DOCUMENTS

| | | | |
|---|---|---|---|
| 5,634,467 | A | 6/1997 | Nevo |
| 5,743,267 | A * | 4/1998 | Nikolic et al. ............. 600/483 |
| 5,758,652 | A | 6/1998 | Nikolic |
| 5,819,735 | A | 10/1998 | Mansfield et al. |
| 5,904,708 | A | 5/1999 | Goedeke |
| 6,090,047 | A | 7/2000 | Kass et al. |
| 6,104,949 | A | 8/2000 | Pitts Crick et al. |
| 6,155,267 | A | 12/2000 | Nelson |
| 6,275,707 | B1 | 8/2001 | Reed et al. |
| 6,280,409 | B1 | 8/2001 | Stone et al. |
| 6,309,350 | B1 | 10/2001 | VanTassel et al. |
| 6,334,849 | B1 | 1/2002 | Sunagawa |
| 6,438,408 | B1 * | 8/2002 | Mulligan et al. ........... 600/510 |
| 6,440,078 | B1 | 8/2002 | Curiel et al. |

OTHER PUBLICATIONS

Milnor, W.R., "Arterial Impedance as Ventricular Afterload," *Circulation Research*, vol. 36, No. 5, p. 565–70 (May 1975).

O'Rourke, M., "Coupling Between the Left Ventricle and Arterial System in Hypertension," *Eur. Heart J.*, vol. 11(G), pp. 24–28 (1990).

Schroff, S.G. et al., "Left Ventricular Systolic Dynamics in Terms of its Chamber Mechanical Properties," *Am J. Physiol*, vol. 245, pp. H110–124 (1983).

Starling, M.R., "Left Ventricular–arterial Coupling Relations in the Normal Human Heart," *Am. Heart J.*, vol. 125, p. 1659–66 (Jun. 1993).

Wesseling et al., "Computation of Aortic Flow from Pressure in Humans using a Non–linear, Three–element Model," *J. Appl. Physiol.*, vol. 74, No. 5, pp. 2566–2573 (1993).

\* cited by examiner

METHODS AND APPARATUS FOR ESTIMATION OF VENTRICULAR AFTERLOAD BASED ON VENTRICULAR PRESSURE MEASUREMENTS

FIELD OF THE INVENTION

This invention relates to methods and apparatus for estimating ventricular afterload presenting resistance to ejection of blood from a ventricle during a blood ejection phase of the ventricle from measurements of ventricular pressure, and in particular for assessing heart failure state from acute or chronically accumulated estimates of ventricular afterload preferably by an implantable medical device (IMD).

BACKGROUND OF THE INVENTION

Almost any cardiac disorder that impairs the ability of the ventricle to eject blood suffers a progression toward an inexorable deterioration of cardiac structure and function, producing the complex clinical syndrome of heart failure (HF), which is a common medical condition that afflicts approximately 1.5 to 2.0% of the population (4.8 million people in the United States) and which has a risk of death of 5 to 10% annually in patients with mild symptoms and increases to as high as 30 to 40% annually in patients with advanced disease, as, set for the in U.S. Pat. No. 6,440,078.

In recent years, physicians have prescribed implantation of conventional, atrioventricular (AV) synchronous pacing systems, including DDD and DDDR pacing systems, marketed by Medtronic, Inc. and other companies, in certain patients for treatment of HF symptoms. Certain patient groups suffering HF symptoms with or without bradycardia tend to do much better hemodynamically with AV synchronous pacing due to the added contribution of atrial contraction to ventricular filling and subsequent contraction. However, fixed or physiologic sensor driven rate responsive pacing in such patients does not always lead to improvement in cardiac output and alleviation of the symptoms attendant to such disease processes because it is difficult to assess the degree of compromise of cardiac output caused by HF and to determine the pacing parameters that are optimal for maximizing cardiac output, particularly the AV delay. Determining an optimal AV delay requires performing echocardiography studies or obtaining pressure data involving an extensive patient work-up as set forth in commonly assigned U.S. Pat. No. 5,626,623.

Data from external Holter monitors can determine if there is any accompanying electrical instability or arrhythmia. However, such Holter monitors cannot measure blood pressure or other indicia of mechanical heart function. Consequently, implantable physiologic cardiac monitors for monitoring the mechanical and/or electrical heart function have been proposed and, in some cases, implemented for deriving and storing EGM and mechanical performance data over a prolonged time.

In particular, the Medtronic® CHRONICLE® Implantable Hemodynamic Monitor (IHM) system comprises a CHRONICLE® Model 9520 IHM of the type described in commonly assigned U.S. Pat. No. 5,368,040 coupled with a Model 4328A pressure sensor lead that senses blood pressure within a heart chamber and the EGM of the heart using a pressure sensing transducer of the type disclosed in commonly assigned U.S. Pat. No. 5,564,434. The CHRONICLE® Model 9520 IHM measures absolute blood pressure, and the patient is also provided with an externally worn Medtronic® Model No. 2955HF atmospheric pressure reference monitor of the type described in commonly assigned U.S. Pat. No. 5,819,735 to record contemporaneous atmospheric pressure values.

The CHRONICLE® Model 9520 IHM can be programmed to measure the RV systolic pressure (maximum pressure in a sampling window), RV diastolic pressure (first sample in a sample window), pulse pressure (RV systolic—RV diastolic pressure), pre-ejection interval (PEI), systolic time interval (STI), peak positive and negative dP/dt, estimated pulmonary artery diastolic pressure (ePAD), patient activity level, and heart rate. The pressure parameters are sampled at a sampling rate of 256 samples per second, digitized and stored in memory registers. The samples are taken in a sampling window of each heart cycle of 20 ms through 500 ms following the detection of an R-wave, unless the R-wave occurs earlier. The Model 9520 IHM is programmed and interrogated employing an external Model 9790 programmer or a PC with CHRONICLE® software to accumulate trend data stored in a large FIFO buffer in RAM at a programmable resolution. The buffer can be filled in approximately an hour using the highest resolution or in about two months using the lowest resolution.

The memory buffers of the CHRONICLE® Model 9520 IHM and the externally worn Medtronic® Model No. 2955HF atmospheric pressure reference monitor can be interrogated to telemetry transmit the measured and stored pressure and other data, thereby emptying the buffers, to a nearby Model 9521HF Interactive Remote Monitor for temporary storage of the data. The Model 9521HF Interactive Remote Monitor external medical device periodically transmits accumulated data to a remote data processing center that processes the data to develop trend data that the attending physician can review with other patient data derived in patient examinations and interviews to assess the HF state.

In addition, the IHM system can be used in the clinical setting to make and observe real-time blood pressure and heart rate measurements while the patient is at rest or is exercising on a treadmill. The patient data can be stored in external clinical systems for historic or benchmark comparative uses over time.

Thus, such an IHM system implanted in patients suffering from cardiac arrhythmias or HF can accumulate date and time stamped blood pressure data that can be of use in determining the condition of the heart over an extended period of time and while the patient is clinically tested or is engaged in daily activities. Various other IHM functions and uses of EGM, pressure and other parameter data accumulated in an IHM are disclosed in U.S. Pat. Nos. 5,417,717, 6,104,949, 6,155,267, 6,280,409, 6,275,707, 6,309,350, and 6,438,408, for example. U.S. Pat. No. 5,758,652 describes an implantable absolute blood pressure monitor and method for measuring the heart condition of a patient by utilizing blood pressure signals filtered to remove respiratory effects.

It is estimated that perhaps as many as 20 million individuals in the United States have an asymptomatic impairment of cardiac function and are likely to develop symptoms of chronic HF in the next 1 to 5 years. The early identification and appropriate treatment of such individuals is highly desirable to achieve the greatest impact on individual and public health. One indicia of an early stage of chronic HF comprises ventricular afterload, which has not, to my knowledge been measured employing an IMD.

Ventricular afterload may be defined as the mechanical force opposing ventricular ejection, as for example described by W. R. Milnor, "Arterial Impedance as Ventricular Load" *Circulation Research*, 1975;36:565–70. This mechanical opposition of the flow of the viscous blood through the visco-elastic arterial system has two major mechanical components determined by the mechanical properties of the arterial system including hydraulic resistance and arterial compliance.

Hydraulic resistance is a function of several factors including the smooth muscle tone of the arterial system that determines arterial dimension, the dimensions and patency of the aortic or pulmonic valve, the geometry of the ventricular outflow tract, thickness of the ventricular myocardium, the length of the arterial vessels and the viscosity of the blood. Hydraulic resistance is proportional to ventricular afterload and can be described in general by Poisuelle's law or by Ohm's law, which states that systemic vascular resistance (also referred to as total peripheral resistance) is equal to the difference between mean arterial pressure and central venous pressure divided by cardiac output. Hydraulic resistance is typically estimated clinically by invasive or non-invasive estimates of mean arterial pressure and cardiac output.

Arterial compliance describes the ability of the arterial blood vessels to store a portion of the energy delivered to the arterial system by the ventricles during systole and return that energy to the arterial blood during ventricular diastole in order to maintain diastolic arterial blood pressure and flow. Arterial compliance is inversely proportional to ventricular afterload. Clinical estimates of arterial compliance are difficult to measure. It is occasionally approximated by aortic distensibility, or the change in aortic pressure divided by the change in aortic cross-sectional area. Another estimate of arterial compliance is "effective arterial elastance" as described for example by R .P Kelly et al., in "Effective Arterial Elastance as an Index of Arterial Vascular Load in Humans" *Circulation* 1992;86:513–521. Estimation of this parameter requires measurement of ventricular pressure and volume.

Ventricular afterload, including both arterial resistance and arterial compliance, may also be estimated using lumped or distributed mathematical models such as for example the three-element Windkessel model described by K .H. Wesseling et al., "Computation of Aortic Flow from Pressure in Humans Using a Non-linear, Three-element Model', *J. Appl. Physiol.*, 1993;74:425–35. The mathematical solution to these models requires measurement of both aortic blood pressure and flow.

The term "ventricular arterial coupling" describes the mechanical relationship between the ventricles and the arterial system during ventricular ejection as described for example by M .R. Starling, "Left Ventricular-arterial Coupling Relations in the Normal Human Heart", *Am. Heart J.*, 1993;125:1659–66. Cardiovascular function may be maintained even if ventricular contractile function is reduced by a compensatory decrease in ventricular afterload (either by decreased resistance, increased compliance or both). For example, administration of nitroglycerin during an episode of myocardial ischemia can maintain cardiac output despite decreased ventricular contractility by reducing arterial tone, increasing arterial compliance and hence decreasing ventricular afterload. Measurement of ventricular arterial coupling parameters involves measurement of both ventricular pressure and volume.

Regional or global changes in ventricular afterload including arterial resistance and compliance may alter patterns of arterial wave reflection. These changes in arterial wave reflection patterns may be manifest by changes in pressure signals measured in the arteries or ventricles as demonstrated for example by M. O'Rourke, "Coupling Between the Left Ventricle and Arterial System in Hypertension", *Eur. Heart J.* 1990;11(G):24–28. Thus, changes in the morphometry of ventricular or arterial blood pressure signals can indicate changes in the resistive and compliant properties of the arterial system and hence can indicate changes in ventricular afterload.

The core of the altered cardiovascular function in HF is a depression of cardiac contractility. Therefore, an adequate assessment of cardiovascular function, including right or left ventricular afterload, has important diagnostic and therapeutic implications. Patients with acute HF, particularly as a complication of acute myocardial infarction or as an acute exacerbation of a previously compensated chronic HF, have a high mortality rate of about 30% within the first 12 months. In this clinical condition, a proper evaluation of ventricular afterload is extremely important for diagnostic purposes to assess the severity of the process and as a guide for the inotropic, vasodilator, or diuretic therapy. Typically, resistance indices are used to evaluate ventricular afterload, such as systolic arterial blood pressure, systemic vascular resistance or peak ventricular wall stress, with the serious limitations that these parameters have, since they ignore arterial compliance. Ventricular afterload may be estimated using aortic (or pulmonary) input impedance. However, this index requires the measurement of both pressure and flow and is difficult to interpret clinically.

Multiple clinical pathologies may result in acute or chronic changes in ventricular afterload including valvular disease, hypertension, ventricular hypertrophy, hypertrophic cardiomyopathy, atherosclerotic plaque formation, arterial thrombus, systemic shock, etc. In addition any vasoactive substance that affects arterial or venous tone, such as but not limited to nitro-glycerin, sodium nitro-prusside, neosynephrine, or epinephrine, can dramatically alter ventricular afterload. Hence, the ability to monitor and minimize ventricular afterload by minimizing arterial resistance, maximizing arterial compliance and controlling the timing of reflected waves by pharmacological or other methods is extremely important.

BRIEF SUMMARY OF THE INVENTION

Therefore, it may be observed from the state of the art that cardiovascular function, or the ability of the heart and vasculature to provide the nutritional needs of all the peripheral tissues, depends on the complex interaction of four distinct mechanical systems. These include the visco-elastic mechanical properties of the veno-atrial (or preload) system), the diastolic mechanical properties of the ventricles, the systolic mechanical properties of the ventricles, and the visco-elastic properties of the arterial (or ventricular afterload) system.

The present invention is therefore directed to methods and apparatus for developing estimates of the ventricular afterload derived from ventricular pressure measurements. The estimates of the ventricular afterload may be used to quantify the current state of cardiovascular function, to discern changes in the state of cardiovascular function over time, and to select or alter a therapy delivered by an IMD to optimize cardiovascular function of patients experiencing heart failure, hypertension and other clinical pathologies as described above.

In accordance with the present invention, certain estimates of ventricular afterload are derived from certain measured absolute right or left ventricular blood pressure values and from the derivatives of certain measured absolute right or left ventricular blood pressure values. In particular, during each ventricular contraction, the ventricular blood pressure waveform is sampled and digitized at a predetermined sampling rate. The sampled pressure data values are processed and compared in real time to determine the peak positive pressure $P_b$ among the sampled pressure values, the peak positive derivative pressure $dP/dt_{PP}$, and the peak negative derivative pressure $dP/dt_{PP}$ of the pressure waveform. The sample time ($t_b$) associated with the sampled peak positive pressure $P_b$, the sample time ($t_a$) associated with the peak positive derivative pressure $dP/dt_{PP}$, and the sample time ($t_c$) associated with the peak negative derivative pressure $dP/dt_{PP}$ of the pressure beat are determined. The absolute blood pressure at time $t_c$ is also determined as pressure $P_c$.

An index $\alpha$ of the relative timing of peak positive pressure $P_b$ is determined by calculating $\alpha=(t_b-t_a)/(t_c-t_a)$. This index $\alpha$ of the relative timing of peak positive pressure $P_b$ does not "calculate" a pressure value. The value of the index $\alpha$ of the relative timing of peak positive pressure $P_b$ is proportional to ventricular afterload and is limited to values between 0 and 1.

When ventricular pressure decreases throughout the ejection phase due to normally high arterial compliance, the peak ventricular pressure $P_b$ occurs early during ejection and $\alpha$ approaches 0, signifying low ventricular afterload. Conversely, when the decrease in ventricular pressure throughout the ejection phase is impeded or slowed by low arterial compliance, the peak ventricular pressure occurs later during ejection and $\alpha$ approaches 1, signifying high ventricular afterload.

An index $\beta$ of the slope of the early ejection pressure is determined by calculating $\beta=(P_c-P_b)/(t_c-t_b)$. This index $\beta$ describes the approximate linear slope of the descent of ventricular pressure from peak pressure $P_b$ to $P_c$. The magnitude of the index $\beta$ is proportional to ventricular afterload. That is, a higher magnitude of the index $\beta$ implies a higher ventricular afterload. The magnitude of the index $\beta$ has no upper limit.

Thus, index $\alpha$ of the relative timing of peak positive pressure $P_b$ and the index $\beta$ of the slope of the early ejection pressure are two independent and alternative, but interrelated methods of quantifying ventricular afterload from right or left ventricular pressure measurements.

In a monitoring context, each index is stored in memory within the IMD for uplink telemetry transmission at a later time to an external medical device for analysis. The changes in ventricular afterload in response to drug or electrical stimulation therapies prescribed to reduce HF or hypertension symptoms, for example, can be assessed from changes in index $\alpha$ of the relative timing of peak positive pressure $P_b$ and the index $\beta$ of the slope of the early ejection pressure.

In a therapy delivery context, a drug therapy or a therapy delivered by an IMD would be changed so as to minimize the indices $\alpha$ and/or $\beta$. For example, a pacing mode or pacing parameter of an implantable pacing system providing single chamber pacing or dual chamber pacing or right and left heart pacing can be varied so that indices $\alpha$ and/or $\beta$ can be determined and compared to determine the optimal pacing rate that results in the minimal values of the indices $\alpha$ and/or $\beta$.

The estimates of the ventricular afterload are advantageously derived from ventricular pressure measurements made by an IMD. However, it will be understood that the indices of the ventricular afterload derived from ventricular pressure measurements can be advantageously performed acutely to diagnose patients employing temporarily implanted pressure measurement instruments.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS OF THE INVENTION

In the following detailed description, references are made to illustrative embodiments for carrying out the invention. It is understood that other embodiments may be utilized without departing from the scope of the invention. An embodiment of the invention is disclosed in detail in the context of an exemplary IMD that is modified to estimate the index $\alpha$ of the relative timing of peak positive pressure $P_b$ and the index $\beta$ of the slope of the early ejection pressure indicative of HF state of a patient's heart employing one or more blood pressure sensor to make pressure measurements within the right or left ventricle.

It will be appreciated from the following description that an IMD incorporating the present invention may be utilized to obtain and store the aforementioned indices along with other patient data over a period of time. The treating physician is able to initiate uplink telemetry of the stored patient data in order to review it to make an assessment of the HF state of the patient's heart from the estimated index data collected over time. The physician can then determine whether a particular therapy is appropriate, prescribe the therapy for a period of time while again accumulating the stored patient data for a later review and assessment to determine whether the applied therapy is beneficial or not, thereby enabling periodic changes in therapy, if appropriate.

The illustrated embodiment of the invention is embodied in an IHM but can be incorporated into therapy delivery IMDs as noted above, e.g., an AV sequential, bi-atrial and bi-ventricular, pacing system operating in demand, atrial tracking, and triggered pacing for restoring synchrony in depolarization and contraction of left and right ventricles in synchronization with atrial sensed and paced events for treating HF and/or bradycardia. The embodiments of the invention can therefore comprise multi-chamber pacing systems programmable to operate as a two, three or four channel pacing system having an AV synchronous operating mode for restoring upper and lower heart chamber synchronization and right and left atrial and/or ventricular chamber depolarization synchrony. Additional therapies include drug therapies and other electrical stimulation therapies, including PESP stimulation. Moreover, in patients prone to malignant tachyarrhythmias, the assessment of HF state can be taken into account in setting parameters of detection or classification of tachyarrhythmias and the therapies that are delivered.

Figure 1:
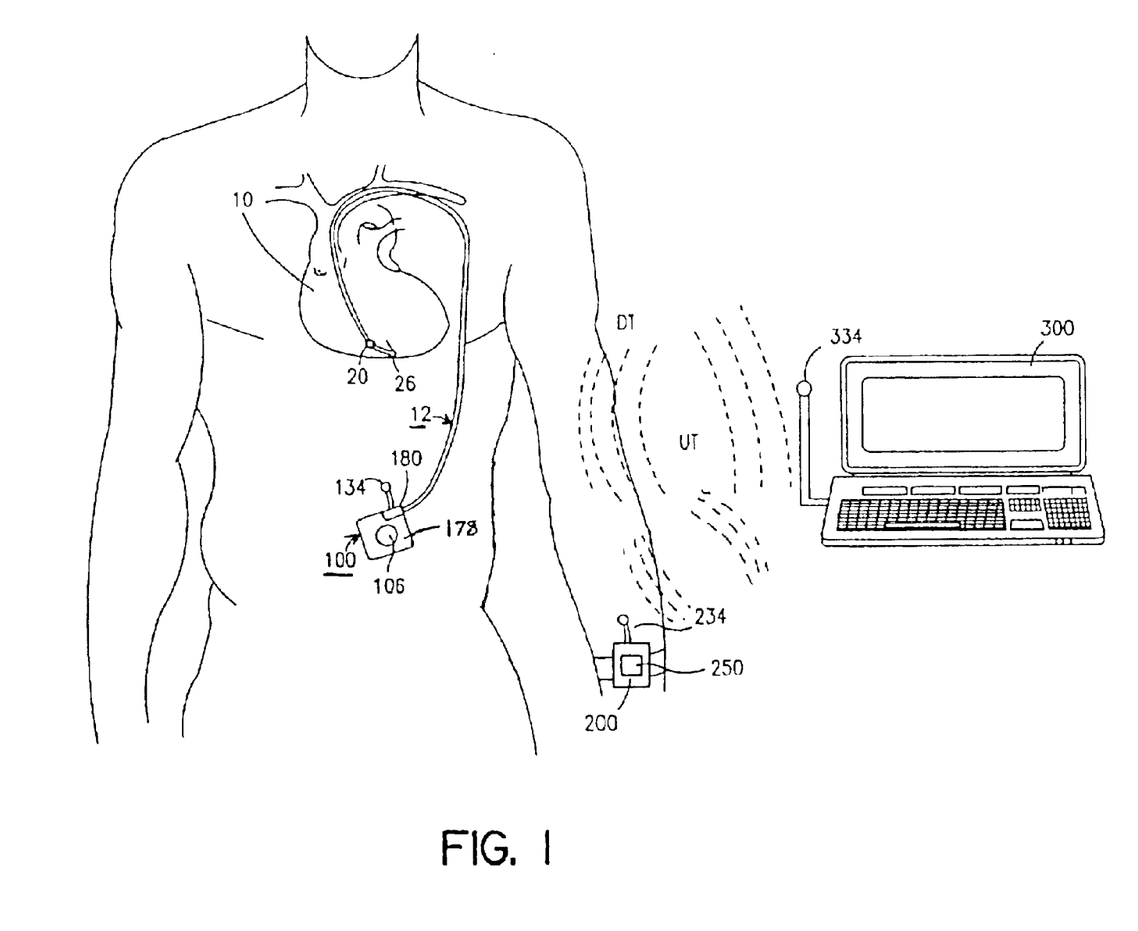
FIG. 1 is a schematic diagram of an exemplary system in which the present invention is preferably implemented.
Figure 2:
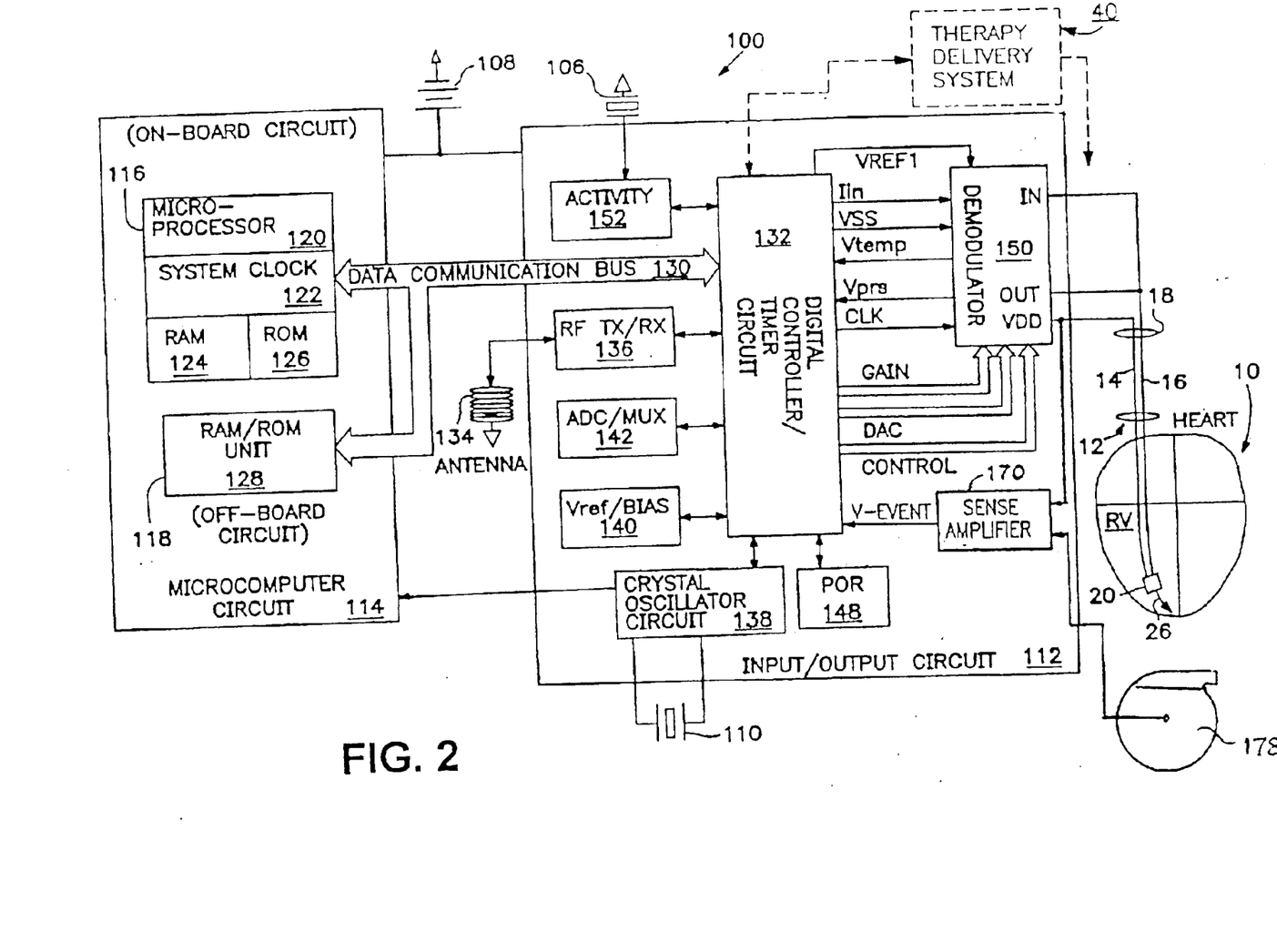
FIG. 2 is a simplified block diagram of one embodiment of IMD circuitry and associated leads employed in the system of FIG. 1 enabling monitoring of blood pressure variables from ventricular blood pressure to determine one or more estimated index related to ventricular afterload in accordance with the present invention.

The exemplary system illustrated in FIGS. 1 and 2 comprises an exemplary IMD 100 and blood pressure lead 12 locating a blood pressure sensor 20 within the right ventricle near the outflow tract of the patient's heart 10. The exemplary system further comprises an externally worn or otherwise carried atmospheric pressure reference monitor 200 to record contemporaneous atmospheric pressure values, and an external programmer 300. External programmer 300 is used to communicate with the IMD 100 and the atmospheric pressure reference monitor 200 in order to program the operating modes and parameters of IMD 100 or interrogate the data stored in memory of the IMD 100 and atmospheric pressure reference monitor 200.

The IMD 100 preferably comprises the above-referenced Medtronic® CHRONICLE® Model 9520 IHM having the capabilities of deriving and storing the above-referenced pressure data as well as heart rate data from the sensed ventricular EGM and patient activity level as monitored by an activity sensor 106. The pressure sensor lead 12 preferably comprises the above-referenced Model 4328A pressure sensor lead that senses blood pressure using a pressure sensing transducer 20 of the type disclosed in commonly assigned U.S. Pat. No. 5,564,434. The pressure sensor lead 12 also incorporates a distal EGM sense electrode 26 and conventional soft pliant tines that provide passive fixation of the sense electrode 26 into the ventricular apex in a manner well known in the art. The proximal connector assembly of pressure sensor lead 12 is configured in conformance with IS-1 standards for bipolar pacing leads and is fitted into a conforming bore of the connector header 180 or IMD 100 in the conventional manner. The EGM of the heart, particularly the R-waves of the PQRST complex, is sensed between the active distal tip electrode 26 and the indifferent electrode formed by the hermetically sealed housing or can 178 of IMD 100 in a conventional unipolar configuration. It will be understood that other possible configurations of the IMD 100 can provide cardioversion/defibrillation and/or pacing therapies requiring additional implantable cardiac leads and electrodes preferably for synchronously pacing upper and lower and right and left heart chambers for improving cardiac output in patients suffering from HF.

The CHRONICLE® Model 9520 IHM measures absolute blood pressure, and so the patient is also provided with the atmospheric pressure reference monitor 200, e.g., the above-referenced Medtronic® Model No. 2955HF atmospheric pressure reference monitor. Atmospheric pressure reference monitor 200 is schematically depicted as worn on the patient's wrist, optionally including a timepiece function 250, but it may take other portable configurations so that it can accompany the patient in the patient's daily routine. The functions of an exemplary atmospheric pressure reference monitor 200 in relation to the IHM 100 and programmer 300 are disclosed in commonly assigned U.S. Pat. No. 5,904,708.

The derivation and storage of atmospheric pressure values by the atmospheric pressure reference monitor 200 are not necessary to practice the present invention, since the above-identified time points and relative pressure values are sufficient to solve the equations for estimating the indices $\alpha$ and $\beta$. The index $\alpha$ of the relative timing of peak positive pressure $P_b$ and the index $\beta$ of the slope of the early ejection pressure can be derived directly from the sampled right and left ventricular pressure signals. However, the estimation of the index $\alpha$ of the relative timing of peak positive pressure $P_b$ and the index $\beta$ of the slope of the early ejection pressure can be performed using the above-identified IHM 100 in a system that happens to also include the atmospheric pressure reference monitor 200.

Uplink telemetry (UT) and downlink telemetry (DT) transmissions between an RF telemetry antenna 134 of the IMD 100 (schematically illustrated as extending from the connector 180 of the IMD 100) and a telemetry antenna 334 of the external programmer 300 are schematically illustrated in FIG. 1. Similarly, UT and DT transmissions between an RF telemetry antenna 234 of the atmospheric pressure reference monitor 200 and the telemetry antenna 334 of the external programmer 300 are also illustrated in FIG. 1. It will be understood that a direct cable or plug-in connection can be made between ports of the atmospheric pressure reference monitor 200 and the external programmer 300 instead of employing the depicted UT and DT transmissions between the RF telemetry antennas 234 and 334 when atmospheric pressure data is to be read from memory in the atmospheric pressure reference monitor 200. The RF telemetry system preferably operates at a long range of about 2 meters or more in a relatively high frequency range. For convenience of description, the preferred embodiment is described as follows using long range RF telemetry transmission, but the invention and following claims are not be interpreted as so limited. Similarly, the terms "telemeter", "telemetry transmission" and the like are intended to embrace any such action and manner of conveying data and commands between the IMD 100, the atmospheric pressure reference monitor 200, and the external programmer 300 or other monitoring device.

In conventional use of the system depicted in FIG. 1, the storage of absolute blood pressure data and ambient pressure data continues for a period of days and the data is periodically transmitted to the external programmer 300 during a telemetry session initiated by medical personnel operating the external programmer 300. The ambient pressure is employed to correct the absolute pressure data.

As noted above, the absolute pressure data that is processed in accordance with the present invention to estimate the indices α and/or β does not require such correction. The present invention is preferably implemented in a system as depicted in FIGS. 1 and 2 operating in accordance with the flow charts of FIG. 3 to derive the indices α and/or β from beat-to-beat blood pressure samples and associated time data without use of the ambient pressure data. The pressure values are processed and compared in real time to determine the peak positive pressure $P_b$, the peak positive derivative pressure $dP/dt_{PP}$, and the peak negative derivative pressure $dP/dt_{NP}$ of the pressure beat. The sample time ($t_b$) associated with the sampled peak positive pressure $P_b$, the sample time ($t_a$) associated with the peak positive derivative pressure $dP/dt_{PP}$, and the sample time ($t_c$) associated with the peak negative derivative pressure $dP/dt_{NP}$ of the pressure beat are also determined. The absolute blood pressure at time $t_c$ is also determined as pressures $P_c$.

FIG. 2 is a simplified block diagram of the pressure sensing lead 12 and the IMD 100 in relation to patient's heart 10. The lead 12 has first and second lead conductors 14 and 16 extending from the connector 180 to the blood pressure sensor 20 disposed near the distal fixation mechanism 26 and to the distal tip sense electrode 26. The blood pressure sensor 20 preferably includes a variable pickoff capacitor and a fixed reference capacitor and signal modulating circuit described in detail in the above-incorporated, commonly assigned, '434 and '752 patents that develops both blood pressure and temperature time-modulated intervals that are decoded as blood pressure and temperature signal values in demodulator 150. The proximal end of lead 12 is formed as a conventional bipolar, in-line pacing lead connector and is coupled to the monitor connector 180 which is formed as a conventional bipolar in-line pacemaker pulse generator connector block assembly.

The circuitry of IMD 100 is powered by battery 108 and generally comprises a microcomputer 114 coupled through data communication bus 130 with an input/output circuit 112 that is coupled to the activity sensor 106, the telemetry antenna 134, the lead conductors 14, 16, and a crystal 110. The input/output circuit 112 includes the digital controller/timer circuit 132 and the associated components including the crystal oscillator 138, power-on-reset (POR) circuit 148, Vref/BIAS circuit 140, ADC/MUX circuit 142, RF transmitter/receiver circuit 136, optional activity circuit 152 and pressure signal demodulator 150.

Crystal oscillator circuit 138 and crystal 110 provide the basic timing clock for the digital controller/timer circuit 132. Vref/BIAS circuit 140 generates stable voltage reference Vref and current levels from battery 108 for the circuits within the digital controller/timer circuit 132, and the other identified circuits including microcomputer 114 and demodulator 150. Power-on-reset circuit 148 responds to initial connection of the circuitry to the battery 108 for defining an initial operating condition and also resets the operating condition in response to detection of a low battery voltage condition. Analog-to-digital converter (ADC) and multiplexor circuit 142 digitizes analog signals Vprs and Vtemp received by digital controller/timer circuit 132 from demodulator 150 for storage by microcomputer 114.

ADC/MUX circuit 142 multiplexes data signals transmitted out through RF transmitter/receiver circuit 136 during telemetry. Voltage reference and bias circuit 140, ADC/MUX circuit 142, POR circuit 148, crystal oscillator circuit 138 and optional activity circuit 152 may correspond to any of those presently used in currently marketed cardiac pacemaker IPGs.

The digital controller/timer circuit 132 includes a set of timers and associated logic circuits connected with the microcomputer 114 through the data communications bus 130. Microcomputer 114 contains an on-board chip including microprocessor 120, associated system clock 122, and on-board RAM and ROM chips 124 and 126, respectively. In addition, microcomputer 114 includes an off-board circuit 118 including separate RAM/ROM chip 128 to provide additional memory capacity. Microprocessor 120 is interrupt driven, operating in a reduced power consumption mode normally, and awakened in response to defined interrupt events, which may include the periodic timing out of data sampling intervals for storage of monitored data, the transfer of triggering and data signals on the bus 130 and the receipt of programming signals. A real-time clock and calendar function may also be included to correlate stored data, particularly the indices α and/or β, to time and date.

Microcomputer 114 controls the operating functions of digital controller/timer 132, specifying which timing intervals are employed, and controlling the duration of the various timing intervals, via the bus 130. The specific current operating modes and interval values are programmable. The programmed-in parameter values and operating modes are received through the antenna 134, demodulated in the RF transmitter/receiver circuit 136 and stored in RAM/ROM chip 128.

Data transmission to and from the external programmer 300 of FIG. 1 is accomplished by means of the telemetry antenna 134 and the associated RF transmitter and receiver 136, which serves both to demodulate received DT transmissions and to UT transmit data to the external programmer 300. A number of power, timing and control signals described in greater detail in the above-incorporated, commonly assigned, '434 and '752 patents are supplied by the digital controller/timer circuit 132 to the demodulator 150 to initiate and power the operation of the blood pressure sensor 20 and selectively read out the pressure and temperature signals Vprs and Vtemp. An active lead conductor 16 is attached through the connector block terminals to input and output terminals of demodulator 150 that supplies a voltage VREG at the output terminal. A passive lead conductor 14 is coupled through to the VDD supply terminal of the demodulator 150. The voltage signals Vprs and Vtemp, developed from intervals between current pulses received at the input terminal, are provided by demodulator 150 to the digital controller/timer circuit 132. The voltage signals Vprs and Vtemp are digitized in an ADC/MUX circuit 142 and stored temporarily in RAM/ROM chip 128 in a manner well known in the art.

Thus, the IMD 100 functions as an implantable physiologic signal sensor, specifically for monitoring and storing digitized blood pressure and temperature data derived from the absolute pressure and temperature sensor 20. The patient activity and EGM data can also be stored. The EGM of the heart, particularly the R-wave of the PQRST complex, is sensed between the active distal tip electrode 26 and the indifferent electrode formed by the hermetically sealed housing or can 178 of IMD 100 by sense amplifier 170 in a conventional unipolar sensing configuration. The sense amplifier 170 declares a V-EVENT when the R-wave is sensed, and the V-EVENT is supplied to the digital controller/timer circuit 132 and functions as an interrupt to the microprocessor 120 in a manner well known in the art.

FIG. 2 also shows the configuration of a therapy delivery device by inclusion of the therapy delivery system block 40 shown in broken lines. The particular therapy delivery system 40 may include one or more of the systems described above, e.g., a single or dual chamber pacing system of the type disclosed in the above-referenced '623 patent, for example.

In accordance with the present invention, the digital controller and timer circuit 132 includes a pressure signal processor of the type disclosed in the above-referenced '040 patent and a real time clock that are employed to derive the peak positive pressure $P_b$, the peak positive derivative pressure $dP/dt_{PP}$, and the peak negative derivative pressure $dP/dt_{NP}$ from the sampled and digitized $V_{prs}$ signals of each pressure beat. The sample times $t_b$, $t_a$, and the sample time $t_c$ are also determined by the pressure signal processor in digital controller and timer circuit 132. The determination of sample times $t_a$, $t_b$, and $t_c$ can be made by reference to a time $t_0$ at the V-EVENT declared preceding the pressure signal measurements. The absolute blood pressure at times $t_a$ and $t_c$ are also determined as pressures $P_a$ and $P_c$, respectively.

These digitized values and sample times are temporarily stored in dedicated storage registers or in RAM in RAM/ROM unit 128. The microcomputer 116 is triggered by a V-EVENT or other interrupt associated with the ventricular contraction to make the calculations of the estimates of the indices α and/or β of ventricular afterload from the stored values and times in accordance with the equations:

$$\alpha=(t_b-t_a)/(t_c-t_a)$$

$$\beta=(P_b-P_c)/(t_b-t_c)$$

The calculations can be made during the heart cycle ending with the next V-EVENT.

Figure 3:
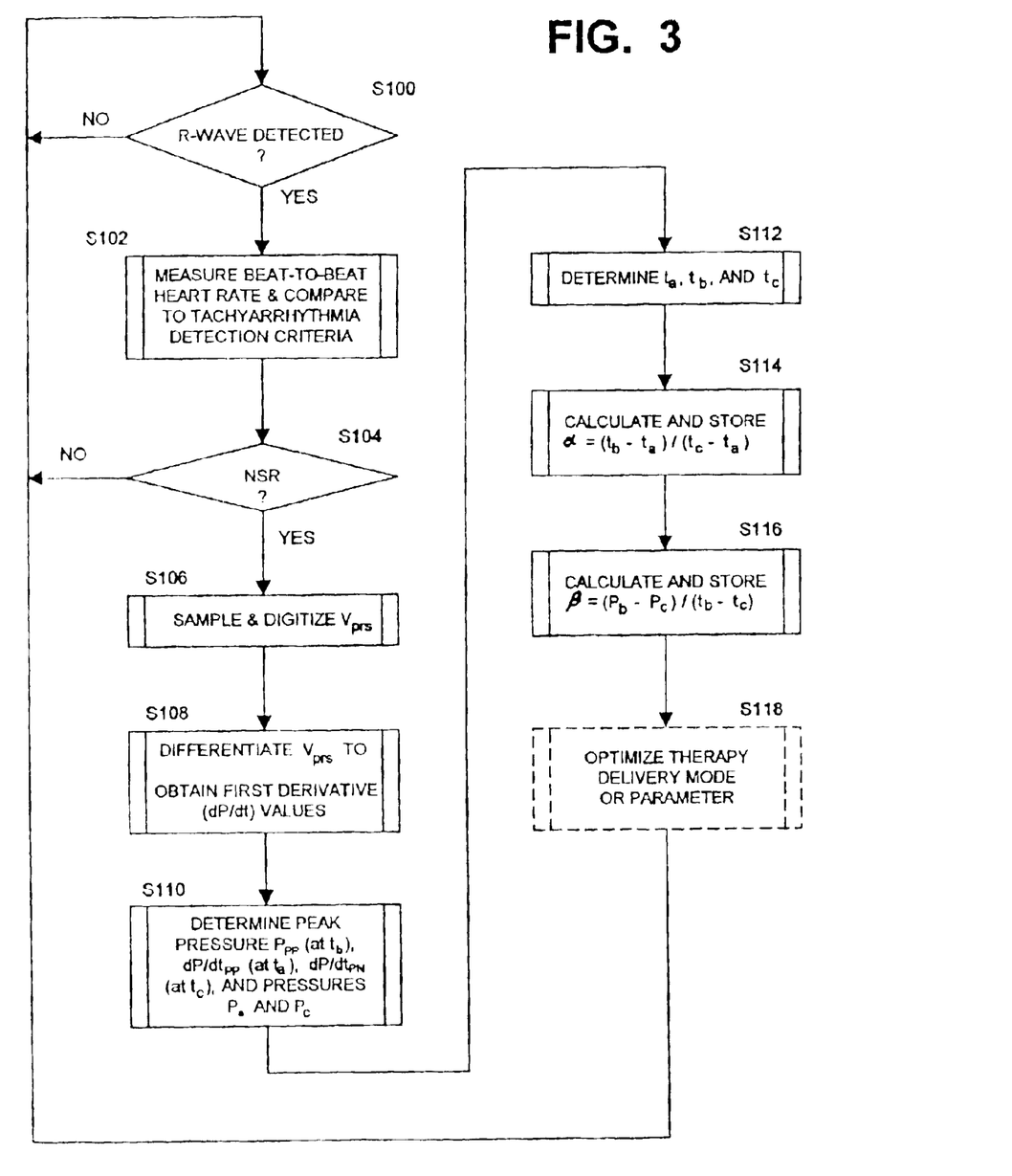
FIG. 3 is a flow chart depicting the steps of determining the indices $\alpha$ and $\beta$ pf ventricular afterload during a ventricular blood pressure wave accompanying a ventricular contraction.

The collection of such blood pressure data points and calculation of the indices α and β is illustrated in FIG. 3. Steps S100–S104 depict the detection of a normal sinus rhythm (NSR) R-wave resulting in declaration of a V-EVENT in FIG. 2, and steps S106–S116 depict the processing of the digitized $V_{prs}$ and associated time data in accordance with the present invention. The storage of the calculated indices α and β in steps S114 and S116 can be facilitated to accommodate available memory by compression of the index values to illustrate trends or by storing only one index determined each day or by storage of a running mean of the calculated indices α and β.

In NSR, the R-wave is sensed across the ventricular sense vector defined as shown in FIGS. 1 and 2 prior to the development of the ventricular blood pressure wave, and so a V-EVENT can be employed to enable pressure sensing for a time window following the V-EVENT to thereby reduce current drain of the IMD battery. Therefore, the collection and processing of ventricular blood pressure data in steps S106–S110 and the determination of the indices α and β as depicted in steps S114 and S116 preferably only occur when the heart rate is determined to represent NSR in steps S102 to S104. Moreover, if may be desirable to limit the determination of the indices α and/or β of ventricular afterload to NSR events at a heart rate that is lower than defined tachyarrhythmia heart rates as determined in step S102.

A therapy delivery mode or parameter is optimized in step S118 if the IMD delivers a therapy. The optimization of a therapy mode or parameter involves incrementally adjusting the mode or parameter, repeating steps S100–S116 one or more times to obtain updated values of the indices α and β, determining from the α and β values whether the change reduces or increases ventricular afterload, readjusting the mode or parameter in the direction that exhibits improvement, and repeating steps S100–S116. Step S118 may be automatically conducted periodically, e.g., once per day when the patient is presumed to be at rest, or only conducted in the presence of a physician in real time in a telemetry session with the external programmer 300.

The determination of the indices α and β from exemplary blood pressure waves under a variety of conditions is depicted in FIGS. 4–9. The exemplary blood pressure waves shown in FIGS. 4–9 were plotted from real-time, left or right, as indicated, ventricular pressure measurements obtained from an acutely instrumented, surgically exposed heart of an anesthetized dog. The left ventricular pressure (LVP) measurements were obtained by placing a high fidelity micro-manometer (Millar Instruments, Houston Tex.) in the left ventricle of each heart via a stab wound into the exterior carotid artery. The analog pressure signal from the micro-manometer was digitized at a sampling frequency of 250 Hz using a personal computer equipped with an analog to digital converter and specialized data acquisition and processing software (Sonometrics, Version 3.2.2, Montreal, Canada).

The peak pressure $P_b$ and the $dP/dt$ values were digitally calculated from the digitized ventricular pressure data using the data acquisition and processing software. In certain experiments, a snare was looped and tightened around the proximal descending aorta in order to create an aortic occlusion that increased ventricular afterload by increasing resistance and decreasing arterial compliance. In certain experiments, temporary pacing was administered to the heart in selected pacing modes from a temporary dual chamber pacemaker pulse generator coupled to temporary atrial and ventricular pacing wires sutured to the right atrial appendage and right ventricular apex, respectively.

Figure 4:
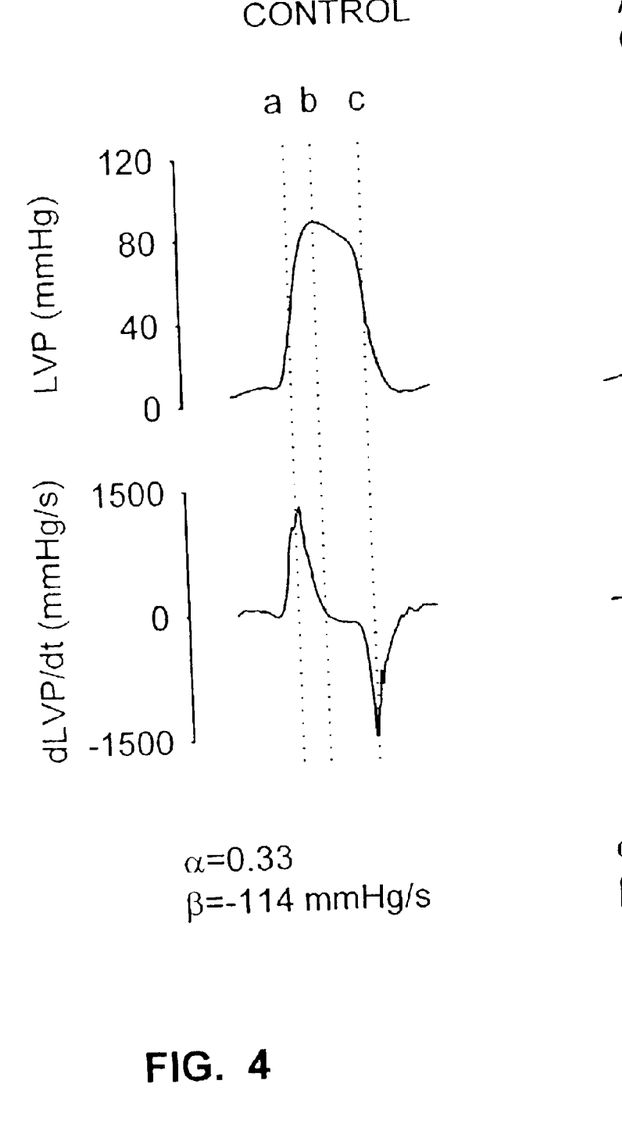
FIG. 4 is a graphical depiction of the determination of the indices $\alpha$ and $\beta$ during a control pressure wave accompanying a control ventricular contraction.
Figure 5:
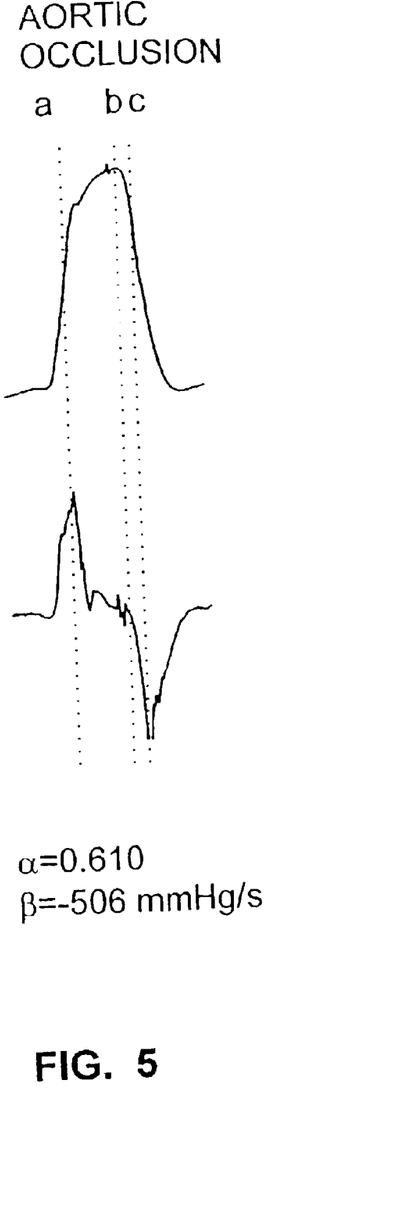
FIG. 5 is a graphical depiction of the determination of the indices $\alpha$ and $\beta$ during a pressure wave accompanying a ventricular contraction while the aorta is occluded.

FIGS. 4 and 5 are graphical depictions of the determination of the indices α and β in steps S114 and S116 from the above-described pressure and time data points derived in steps S106–S110 at points "a", "b" and "c" during a control pressure wave accompanying a control ventricular contraction and during a pressure wave accompanying a ventricular contraction while the aorta is occluded, respectively. In FIG. 4, the index α=0.33 and the index β=−114 mmHg/s, signifying that the ventricular afterload is relatively low. In FIG. 5, the index α=0.61 and the index β=−506 mmHg/s, signifying that the ventricular afterload is increased due, in this example, to the temporary occlusion of the aorta by tightening the snare.

Thus the comparison of the values of α and magnitudes of β derived when the aorta is normal as shown in FIG. 4 or temporarily occluded as shown in FIG. 5 demonstrate that the degree of ventricular afterload affecting a heart can be assessed from the values of α and magnitudes of β. It can be logically deduced that derivation of a value of α and a magnitude of β in a human patient can be of value in assessing the patient's current HF state. Moreover, it follows that repeated derivations and comparisons of values of α and magnitudes of β can be of value in assessing the progression over time of the HF state, hypertension, or other pathologies affecting or associated with ventricular afterload.

Figure 6:
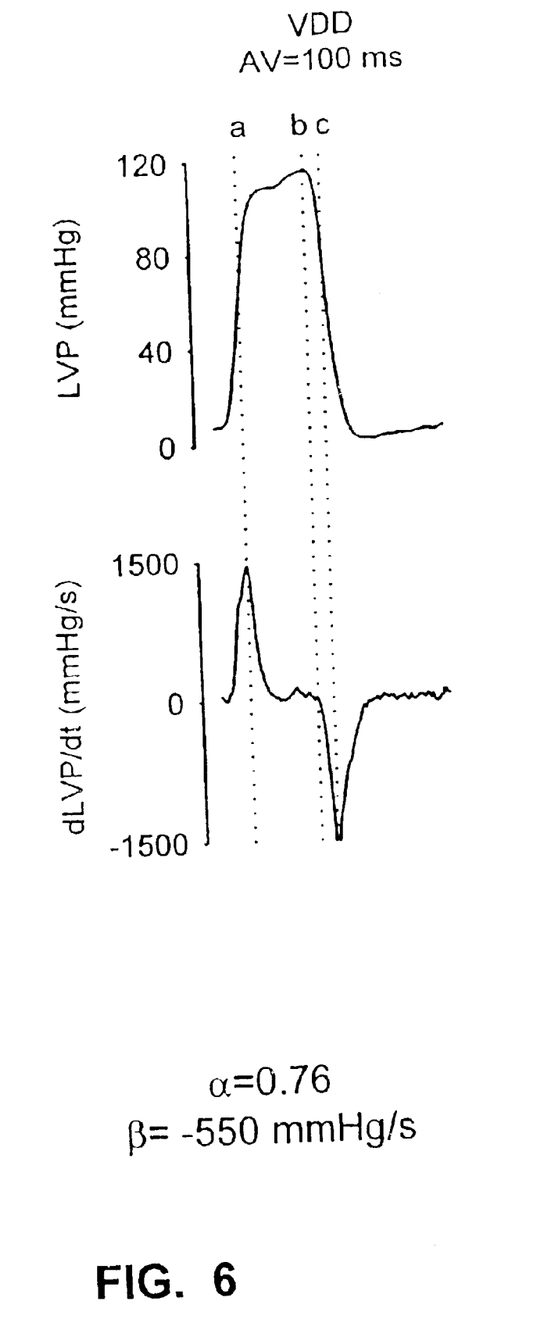
FIG. 6 is a graphical depiction of the determination of the indices $\alpha$ and $\beta$ during a pressure wave accompanying a ventricular contraction while the heart is paced in a VDD pacing mode.

FIG. 6 is a graphical depiction of the determination of the indices α and β in steps S114 and S116 from the above-described pressure and time data points derived in steps S106–S110 at points "a", "b" and "c" of a heart that is being paced in a VDD pacing mode having an AV delay set to 100 ms. In FIG. 6, the index α=0.76 and the index β=−550 mmHg/s, signifying that the ventricular afterload is relatively high and suggesting that the pacing mode or a pacing parameter, e.g., the AV delay, should be changed to reduce the ventricular afterload.

Figure 7:
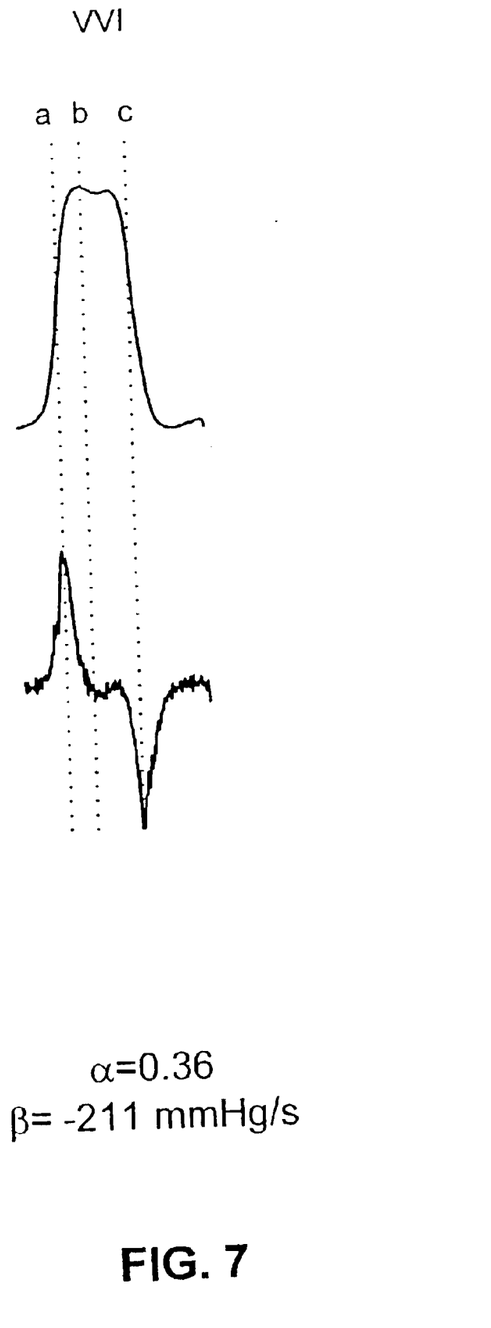
FIG. 7 is a graphical depiction of the determination of the indices $\alpha$ and $\beta$ during a pressure wave accompanying a ventricular contraction while the heart is paced in a VVI pacing mode.

FIG. 7 is a graphical depiction of the determination of the indices α and β in steps S114 and S116 from the above-described pressure and time data points derived in steps S106–S110 at points "a", "b" and "c" of a heart that is being paced in a VVI pacing mode. In FIG. 7, the index α=0.36 and the index β=−211 mmHg/s, signifying that the ventricular afterload is relatively low. In FIG. 7 asynchronous VVI pacing of the right ventricular apex results in less efficient ventricular contraction, again leading to increased ventricular afterload.

The pacing mode experiments were conducted on dog hearts that did not necessarily require pacing and so the pacing escape intervals were selected to provide pacing to capture the heart at paced heart rates that exceeded the intrinsic heart rate. Nevertheless, the examples of FIGS. 6 and 7 suggest that the indices α and β are sensitive to pacing modes and pacing parameters. The examples of FIGS. 6 and 7 also suggest that the pacing mode that might be established for a patient's heart that is pacemaker dependent could negatively affect ventricular afterload. Therefore, the indices α and β could be used in a patient work-up to select the pacing mode and pacing parameters of the selected pacing mode for the patient that minimizes ventricular afterload. Moreover, it follows that repeated derivations and comparisons of values of α and magnitudes of β can be of value in assessing the effect of the pacing mode on the heart over time.

At the present time, chronically implantable pressure sensor bearing leads that are commercially available for implantation are recommended for implantation into the right ventricle or right ventricular outflow tract to make right ventricular pressure measurements as described above in reference to FIGS. 1–3. However, it is understood that these chronically implantable pressure sensor bearing leads function just as well in the left ventricle although such implantation is not explicitly recommended due to possible clot formation and release into the arterial system. Thus, the technology is available to measure LVP.

It is desirable to be able to develop the indices α and β from both RV and LV pressure measurements. Right and left ventricular afterload are independent of one another; that is a patient can exhibit high RV afterload symptomatic of pulmonary hypertension or high LV afterload. High RV afterload is associated with pulmonary hypertension which can lead to right heart failure, right ventricular dilation, RV hypertrophy, tricuspid valve regurgitation, peripheral edema, atrial and ventricular arrhythmias, hypoxia and death. High LV afterload is associated with arterial hypertension, pulmonary edema, mitral valve regurgitation, LV dilation, LV hypertrophy, atrial dilation, atrial arrhythmias, LV failure, ventricular arrhythmias acute ischemia and death.

Figure 8:
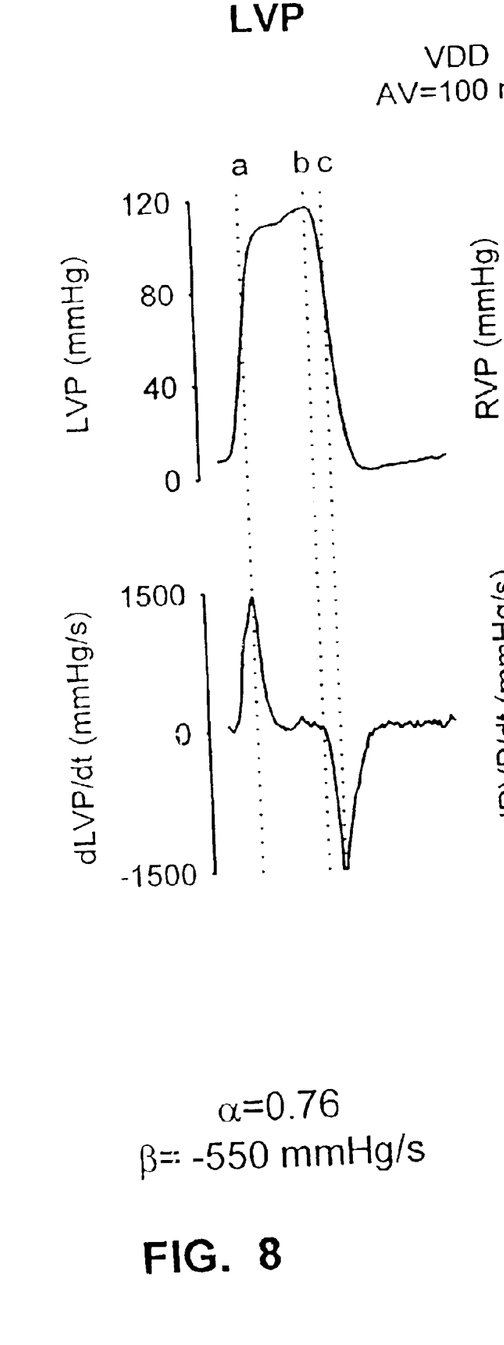
FIG. 8 is a graphical depiction of the determination of the indices $\alpha$ and $\beta$ from left ventricular pressure (LVP) readings during a pressure wave accompanying a ventricular contraction while the heart is paced in a VDD pacing mode.
Figure 9:
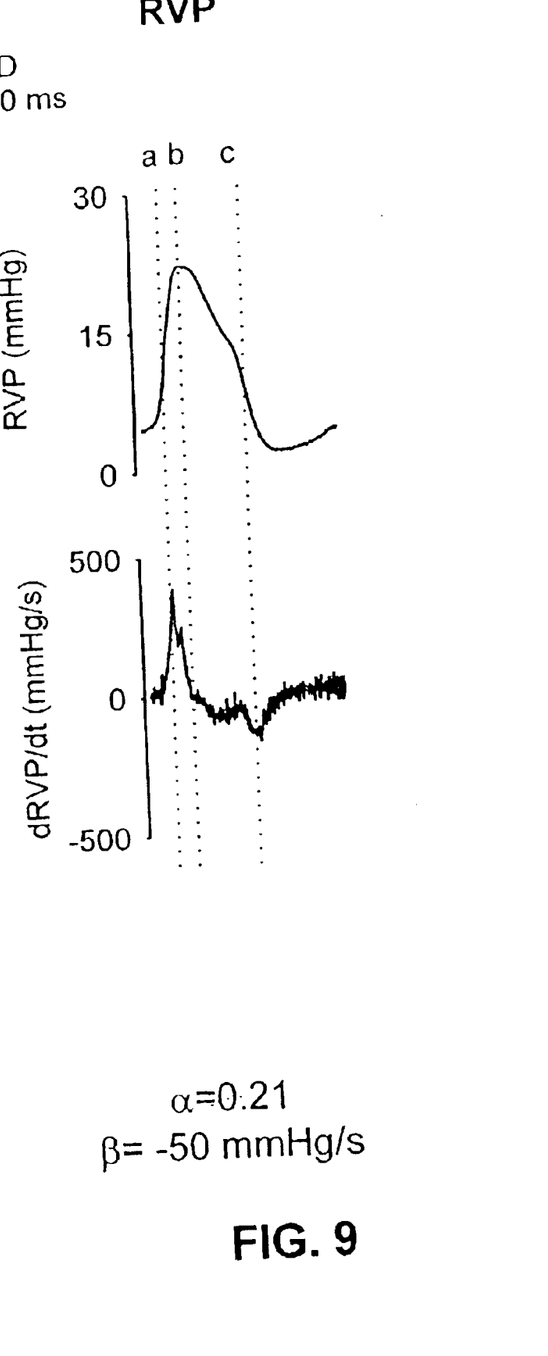
FIG. 9 is a graphical depiction of the determination of the indices $\alpha$ and $\beta$ from right ventricular pressure (RVP) readings during a pressure wave accompanying a ventricular contraction while the heart is paced in a VDD pacing mode.

Therefore, pressure waveforms and data shown in FIGS. 8 and 9 were derived in the acute experiments by placing the above-described micro-manometer in the left and right ventricles, respectively, of a dog heart to derive the left ventricular pressure (LVP) pressure and time data points or right ventricular pressure (RVP) pressure and time data points from which the LVP and RVP indices α and β were determined.

In FIG. 8 (corresponding to FIG. 6) and 9, the dog heart is acutely paced as described above in the VDD pacing mode having an AV delay of 100 ms. In FIG. 8, the pressure $V_{PRS}$ is measured in the left ventricle resulting in the index α=0.76 and the index β=−550 mmHg/s. In FIG. 9, the pressure $V_{PRS}$ is measured in the right ventricle, and the index α=0.21 and the index β=−50 mmHg/s. The wide difference in the LVP and RVP values of α and magnitudes of β signify that, in a healthy dog heart, RV afterload is much lower than LV afterload, as is commonly understood.

In reference to FIG. 3, it can be assumed that the LVP and RVP time data points that are periodically derived in steps S106–S110 at points "a", "b" and "c" and the pressure waveform data that is periodically determined in steps S114 and S116 obtained during the same ejection period in the same heart would differ in the same way as illustrated in FIGS. 8 and 9. Nevertheless, it is expected that the RVP derived values of α and magnitudes of β can be of value to assess current right ventricular afterload, changes in right ventricular afterload determined from chronically accumulated data, and in assessing optimal pacing modes and parameters.

Thus, exemplary methods and apparatus have been described for developing estimates of the ventricular afterload derived from ventricular pressure measurements. The estimates of the ventricular afterload may be used to quantify the current state of cardiovascular function, to discern changes in the state of cardiovascular function over time, and to select or alter a therapy delivered by an IMD to optimize cardiovascular function of patients experiencing heart failure, hypertension and other clinical pathologies as described above.

Furthermore, while the exemplary methods and apparatus have been described for developing estimates of the ventricular afterload derived from ventricular pressure measurements through use of an IMD, it will be understood that the indices of the ventricular afterload derived from ventricular pressure measurements can be advantageously performed acutely to diagnose patients employing temporarily implanted pressure measurement instruments.

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments.

In addition, it will be understood that specifically described structures, functions and operations set forth in the above-referenced patents can be practiced in conjunction with the present invention, but they are not essential to its practice.

It is therefore to be understood, that within the scope of the appended claims, the invention may be practiced otherwise than as specifically described without actually departing from the spirit and scope of the present invention.

What is claimed is:

1. A method of deriving an index of ventricular afterload presenting resistance to ejection of blood from a ventricle during a blood ejection phase comprising:

obtaining a set of ventricular pressure values of blood pressure within a ventricle at sample times during the blood ejection phase of the ventricle;

determining the peak positive pressure value $P_b$, the peak positive derivative pressure $dP/dt_{PP}$ and the peak negative derivative pressure $dP/dt_{NP}$ from the set of ventricular pressure values;

determining the sample time $t_b$ of peak positive pressure, the sample time $t_a$ of the peak positive derivative pressure $dP/dt_{PP}$, and the sample times $t_c$ of the peak negative derivative pressure $dP/dt_{NP}$ from the sample times associated with the set of ventricular pressure values; and calculating an index α of the relative timing of peak positive pressure $P_b$ in the blood ejection phase in accordance with the formula $\alpha=(t_b-t_a)/(t_{c-ta})$, wherein the severity of ventricular afterload is proportional to the value of index α in the range between 0 and 1.

2. The method of claim 1, further comprising:

determining the decreasing pressure $P_c$ associated with the peak negative derivative pressure $dP/dt_{NP}$ from the set of ventricular pressure values; and calculating an index β of the slope of the early ejection pressure in the blood ejection phase in accordance with the formula $\beta=(P_c-P_b)/(t_c-t_b)$, wherein the severity of ventricular afterload is proportional to the magnitude of the index β.

3. The method of claim 2, wherein the obtaining step further comprises obtaining a set of right ventricular pressure values of right ventricular blood pressure within a right ventricle at sample times during the blood ejection phase of the right ventricle.

4. The method of claim 2, wherein the obtaining step further comprises obtaining a set of left ventricular pressure values of left ventricular blood pressure within a left ventricle at sample times during the blood ejection phase of the left ventricle.

5. A method of deriving an index of ventricular afterload presenting resistance to ejection of blood from a ventricle during a blood ejection phase comprising:

obtaining a set of ventricular pressure values of blood pressure within a ventricle at sample times during the blood ejection phase of the ventricle;

determining the peak positive pressure value $P_b$, the peak negative derivative pressure $dP/dt_{NP}$, and the decreasing pressure $P_c$ associated with the peak negative derivative pressure $dP/dt_{NP}$ from the set of ventricular pressure values;

determining the sample time $t_b$ of peak positive pressure, and the sample time $t_c$ of the peak negative derivative pressure $dP/dt_{NP}$ from the sample times associated with the set of ventricular pressure values; and calculating an index β of the slope of the early ejection pressure in the blood ejection phase in accordance with the formula $\beta=(P_c-P_b)/(t_c-t_b)$, wherein the severity of ventricular afterload is proportional to the magnitude of the index β.

6. The method of claim 5, wherein the obtaining step further comprises obtaining a set of right ventricular pressure values of right ventricular blood pressure within a right ventricle at sample times during the blood ejection phase of the right ventricle.

7. The method of claim 5, wherein the obtaining step further comprises obtaining a set of left ventricular pressure values of left ventricular blood pressure within a left ventricle at sample times during the blood ejection phase of the left ventricle.

8. In an implantable heart monitor adapted to be implanted in a patient's body and comprising a pressure sensor coupled with pressure signal processing circuitry and memory for data storage, a method of deriving an index of ventricular afterload presenting resistance to ejection of blood from a ventricle during a blood ejection phase comprising:

operating the pressure sensor to obtain a set of ventricular pressure values of blood pressure within a ventricle at sample times during the blood ejection phase of the ventricle;

determining the peak positive pressure value $P_b$, the peak positive derivative pressure $dP/dt_{PP}$ and the peak negative derivative pressure $dP/dt_{NP}$ from the set of ventricular pressure values;

determining the sample time $t_b$ of peak positive pressure, the sample time $t_a$ of the peak positive derivative pressure $dP/dt_{PP}$, and the sample time $t_c$ of the peak negative derivative pressure $dP/dt_{NP}$ from the sample times associated with the set of ventricular pressure values;

calculating an index α of the relative timing of peak positive pressure $P_b$ in the blood ejection phase in accordance with the formula $\alpha=(t_b-t_a)/(t_c-t_a)$, wherein the severity of ventricular afterload is proportional to the value of index α in the range between 0 and 1; and storing the calculated index α in data storage memory.

9. The method of claim 8, further comprising:

determining the decreasing pressure $P_c$ associated with the peak negative derivative pressure $dP/dt_{NP}$ from the set of ventricular pressure values;

calculating an index β of the slope of the early ejection pressure in the blood ejection phase in accordance with the formula $\beta=(P_c-P_b)/(t_c-t_b)$, wherein the severity of ventricular afterload is proportional to the magnitude of the index β; and storing the calculated index β in data storage memory.

10. The method of claim 8, wherein the obtaining step further comprises obtaining a set of right ventricular pressure values of right ventricular blood pressure within a right ventricle at sample times during the blood ejection phase of the right ventricle.

11. The method of claim 8, wherein the obtaining step further comprises obtaining a set of left ventricular pressure values of left ventricular blood pressure within a left ventricle at sample times during the blood ejection phase of the left ventricle.

12. In an implantable heart monitor adapted to be implanted in a patient's body and comprising a pressure sensor coupled with pressure signal processing circuitry and memory for data storage, a method of deriving an index of ventricular afterload presenting resistance to ejection of blood from a ventricle during a blood ejection phase comprising:

obtaining a set of ventricular pressure values of blood pressure within a ventricle at sample times during the blood ejection phase of the ventricle;

determining the peak positive pressure value $P_b$, the peak negative derivative pressure $dP/dt_{NP}$, and the decreasing pressure $P_c$ associated with the peak negative derivative pressure $dP/dt_{NP}$ from the set of ventricular pressure values;

determining the sample time $t_b$ of peak positive pressure, and the sample time $t_c$ of the peak negative derivative pressure $dP/dt_{NP}$ from the sample times associated with the set of ventricular pressure values; and calculating an index β of the slope of the early ejection pressure in the blood ejection phase in accordance with the formula $\beta=(P_c-P_b)/(t_c-t_b)$, wherein the severity of ventricular afterload is proportional to the magnitude of the index β; and storing the calculated index β in data storage memory.

13. The method of claim 12, wherein the obtaining step further comprises obtaining a set of right ventricular pressure values of right ventricular blood pressure within a right ventricle at sample times during the blood ejection phase of the right ventricle.

14. The method of claim 12, wherein the obtaining step further comprises obtaining a set of left ventricular pressure values of left ventricular blood pressure within a left ventricle at sample times during the blood ejection phase of the left ventricle.

15. The method of claim 12, wherein the implantable medical device adapted to be implanted in the patient's body comprises means for delivering a therapy in accordance with adjustable therapy delivery operating modes and parameters.

16. In an implantable medical device adapted to be implanted in a patient's body for delivering a therapy in accordance with adjustable therapy delivery operating modes and parameters comprising a pressure sensor coupled with pressure signal processing circuitry and therapy delivery means for delivering a therapy, a method of deriving an index of ventricular afterload presenting resistance to ejection of blood from a ventricle during a blood ejection phase comprising:

obtaining a set of ventricular pressure values of blood pressure within a ventricle at sample times during the blood ejection phase of the ventricle;

determining the peak positive pressure value $P_b$, the peak positive derivative pressure $dP/dt_{PP}$ and the peak negative derivative pressure $dP/dt_{NP}$ from the set of ventricular pressure values;

determining the sample time $t_b$ of peak positive pressure, the sample time $t_a$ of the peak positive derivative pressure $dP/dt_{PP}$, and the sample time $t_c$ of the peak negative derivative pressure $dP/dt_{NP}$ from the sample times associated with the set of ventricular pressure values;

calculating an index $\alpha$ of the relative timing of peak positive pressure $P_b$ in the blood ejection phase in accordance with the formula $\alpha=(t_b-t_a)/(t_c-t_a)$, wherein the severity of ventricular afterload is proportional to the value of index $\alpha$ in the range between 0 and 1; and adjusting one of a therapy delivery operating mode or parameter to minimize the value of index $\alpha$.

17. The method of claim 16, further comprising:

determining the decreasing pressure $P_c$ associated with the peak negative derivative pressure $dP/dt_{NP}$ from the set of ventricular pressure values;

calculating an index $\beta$ of the slope of the early ejection pressure in the blood ejection phase in accordance with the formula $\beta=(P_c-P_b)/(t_c-t_b)$, wherein the severity of ventricular afterload is proportional to the magnitude of the index $\beta$; and adjusting one of a therapy delivery operating mode or parameter to minimize the magnitude of index $\beta$.

18. The method of claim 16, wherein the obtaining step further comprises obtaining a set of right ventricular pressure values of right ventricular blood pressure within a right ventricle at sample times during the blood ejection phase of the right ventricle.

19. The method of claim 16, wherein the obtaining step further comprises obtaining a set of left ventricular pressure values of left ventricular blood pressure within a left ventricle at sample times during the blood ejection phase of the left ventricle.

20. In an implantable medical device adapted to be implanted in a patient's body for delivering a therapy in accordance with adjustable therapy delivery operating modes and parameters comprising a pressure sensor coupled with pressure signal processing circuitry and therapy delivery means for delivering a therapy, a method of deriving an index of ventricular afterload presenting resistance to ejection of blood from a ventricle during a blood ejection phase comprising:

obtaining a set of ventricular pressure values of blood pressure within a ventricle at sample times during the blood ejection phase of the ventricle;

determining the peak positive pressure value $P_b$, the peak negative derivative pressure $dP/dt_{NP}$, and the decreasing pressure $P_c$ associated with the peak negative derivative pressure $dP/dt_{NP}$ from the set of ventricular pressure values;

determining the sample time $t_b$ of peak positive pressure, and the sample time $t_c$ of the peak negative derivative pressure $dP/dt_{NP}$ from the sample times associated with the set of ventricular pressure values; and calculating an index $\beta$ of the slope of the early ejection pressure in the blood ejection phase in accordance with the formula $\beta=(P_c-P_b)/(t_c-t_b)$, wherein the severity of ventricular afterload is proportional to the magnitude of the index $\beta$; and adjusting one of a therapy delivery operating mode or parameter to minimize the magnitude of index $\beta$.

21. The method of claim 20, wherein the obtaining step further comprises obtaining a set of right ventricular pressure values of right ventricular blood pressure within a right ventricle at sample times during the blood ejection phase of the right ventricle.

22. The method of claim 20, wherein the obtaining step further comprises obtaining a set of left ventricular pressure values of left ventricular blood pressure within a left ventricle at sample times during the blood ejection phase of the left ventricle.

23. Apparatus that derives an index of ventricular afterload presenting resistance to ejection of blood from a ventricle during a blood ejection phase comprising:

means for obtaining a set of ventricular pressure values of blood pressure within a ventricle at sample times during the blood ejection phase of the ventricle;

means for determining the peak positive pressure value $P_b$, the peak positive derivative pressure $dP/dt_{PP}$ and the peak negative derivative pressure $dP/dt_{NP}$ from the set of ventricular pressure values;

means for determining the sample time $t_b$ of peak positive pressure, the sample time $t_a$ of the peak positive derivative pressure $dP/dt_{PP}$, and the sample time $t_c$ of the peak negative derivative pressure $dP/dt_{NP}$ from the sample times associated with the set of ventricular pressure values; and means for calculating an index $\alpha$ of the relative timing of peak positive pressure $P_b$ in the blood ejection phase in accordance with the formula $\alpha=(t_b-t_a)/(t_c-t_a)$, wherein the severity of ventricular afterload is proportional to the value of index $\alpha$ in the range between 0 and 1.

24. The apparatus of claim 23, further comprising:

means for determining the decreasing pressure $P_c$ associated with the peak negative derivative pressure $dP/dt_{NP}$ from the set of ventricular pressure values; and means for calculating an index $\beta$ of the slope of the early ejection pressure in the blood ejection phase in accordance with the formula $\beta=(P_c-P_b)/(t_c-t_b)$, wherein the severity of ventricular afterload is proportional to the magnitude of the index $\beta$.

25. The apparatus of claim 23, wherein the obtaining means further comprises means for obtaining a set of right ventricular pressure values of right ventricular blood pressure within a right ventricle at sample times during the blood ejection phase of the right ventricle.

26. The apparatus of claim 23, wherein the obtaining means further comprises means for obtaining a set of left ventricular pressure values of left ventricular blood pressure within a left ventricle at sample times during the blood ejection phase of the left ventricle.

27. Apparatus that derives an index of ventricular afterload presenting resistance to ejection of blood from a ventricle during a blood ejection phase comprising:

means for obtaining a set of ventricular pressure values of blood pressure within a ventricle at sample times during the blood ejection phase of the ventricle;

means for determining the peak positive pressure value $P_b$, the peak negative derivative pressure $dP/dt_{NP}$, and the decreasing pressure $P_c$ associated with the peak negative derivative pressure $dP/dt_{NP}$ from the set of ventricular pressure values;

means for determining the sample time $t_b$ of peak positive pressure, and the sample time $t_c$ of the peak negative derivative pressure $dP/dt_{NP}$ from the sample times associated with the set of ventricular pressure values; and means for calculating an index $\beta$ of the slope of the early ejection pressure in the blood ejection phase in accordance with the formula $\beta=(P_c-P_b)/(t_c-t_b)$, wherein the severity of ventricular afterload is proportional to the magnitude of the index $\beta$.

28. The apparatus of claim 27, wherein the obtaining means further comprises means for obtaining a set of right ventricular pressure values of right ventricular blood pressure within a right ventricle at sample times during the blood ejection phase of the right ventricle.

29. The apparatus of claim 27, wherein the obtaining means further comprises means for obtaining a set of left ventricular pressure values of left ventricular blood pressure within a left ventricle at sample times during the blood ejection phase of the left ventricle.

30. In an implantable heart monitor adapted to be implanted in a patient's body and comprising a pressure sensor coupled with pressure signal processing circuitry and memory for data storage, apparatus that derives an index of ventricular afterload presenting resistance to ejection of blood from a ventricle during a blood ejection phase comprising:

means for operating the pressure sensor to obtain a set of ventricular pressure values of blood pressure within a ventricle at sample times during the blood ejection phase of the ventricle;

means for determining the peak positive pressure value $P_b$, the peak positive derivative pressure $dP/dt_{PP}$ and the peak negative derivative pressure $dP/dt_{NP}$ from the set of ventricular pressure values;

means for determining the sample time $t_b$ of peak positive pressure, the sample time $t_a$ of the peak positive derivative pressure $dP/dt_{PP}$, and the sample time $t_c$ of the peak negative derivative pressure $dP/dt_{NP}$ from the sample times associated with the set of ventricular pressure values;

means for calculating an index $\alpha$ of the relative timing of peak positive pressure $P_b$ in the blood ejection phase in accordance with the formula $\alpha=(t_b-t_a)/(t_c-t_a)$, wherein the severity of ventricular afterload is proportional to the value of index $\alpha$ in the range between 0 and 1; and means for storing the calculated index $\alpha$ in data storage memory.

31. The apparatus of claim 30, further comprising:

means for determining the decreasing pressure $P_c$ associated with the peak negative derivative pressure $dP/dt_{NP}$ from the set of ventricular pressure values;

means for calculating an index $\beta$ of the slope of the early ejection pressure in the blood ejection phase in accordance with the formula $\beta=(P_c-P_b)/(t_c-t_b)$, wherein the severity of ventricular afterload is proportioned to the magnitude of the index $\beta$; and means for storing the calculated index $\beta$ in data storage memory.

32. The apparatus of claim 30, wherein the obtaining means further comprises means for obtaining a set of right ventricular pressure values of right ventricular blood pressure within a right ventricle at sample times during the blood ejection phase of the right ventricle.

33. The apparatus of claim 30, wherein the obtaining means further comprises means for obtaining a set of left ventricular pressure values of left ventricular blood pressure within a left ventricle at sample times during the blood ejection phase of the left ventricle.

34. In an implantable heart monitor adapted to be implanted in a patient's body and comprising a pressure sensor coupled with pressure signal processing circuitry and memory for data storage, apparatus that derives an index of ventricular afterload presenting resistance to ejection of blood from a ventricle during a blood ejection phase comprising:

means for obtaining a set of ventricular pressure values of blood pressure within a ventricle at sample times during the blood ejection phase of the ventricle;

means for determining the peak positive pressure value $P_b$, the peak negative derivative pressure $dP/dt_{NP}$, and the decreasing pressure $P_c$ associated with the peak negative derivative pressure $dP/dt_{NP}$ from the set of ventricular pressure values;

means for determining the sample time $t_b$ of peak positive pressure, and the sample time $t_c$ of the peak negative derivative pressure $dP/dt_{NP}$ from the sample times associated with the set of ventricular pressure values;

means for calculating an index $\beta$ of the slope of the early ejection pressure in the blood ejection phase in accordance with the formula $\beta=(P_c-P_b)/(t_c-t_b)$, wherein the severity of ventricular afterload is proportional to the magnitude of the index $\beta$; and means for storing the calculated index $\beta$ in data storage memory.

35. The apparatus of claim 34, wherein the obtaining means further comprises means for obtaining a set of right ventricular pressure values of right ventricular blood pressure within a right ventricle at sample times during the blood ejection phase of the right ventricle.

36. The apparatus of claim 34, wherein the obtaining means further comprises means for obtaining a set of left ventricular pressure values of left ventricular blood pressure within a left ventricle at sample times during the blood ejection phase of the left ventricle.

37. In an implantable medical device adapted to be implanted in a patient's body for delivering a therapy in accordance with adjustable therapy delivery operating modes and parameters comprising a pressure sensor coupled with pressure signal processing circuitry and therapy delivery means for delivering a therapy, apparatus that derives an index of ventricular afterload presenting resistance to ejection of blood from a ventricle during a blood ejection phase comprising:

means for obtaining a set of ventricular pressure values of blood pressure within a ventricle at sample times during the blood ejection phase of the ventricle;

means for determining the peak positive pressure value $P_b$, the peak positive derivative pressure $dP/dt_{PP}$ and the peak negative derivative pressure $dP/dt_{NP}$ from the set of ventricular pressure values;

means for determining the sample time $t_b$ of peak positive pressure, the sample time $t_a$ of the peak positive derivative pressure $dP/dt_{PP}$, and the sample time $t_c$ of the peak negative derivative pressure $dP/dt_{NP}$ from the sample times associated with the set of ventricular pressure values;

means for calculating an index $\alpha$ of the relative timing of peak positive pressure $P_b$ in the blood ejection phase in accordance with the formula $\alpha=(t_b-t_a)/(t_c-t_a)$, wherein the severity of ventricular afterload is proportional to the value of index $\alpha$ in the range between 0 and 1; and means for adjusting one of a therapy delivery operating mode or parameter to minimize the value of index $\beta$.

38. The apparatus of claim 37, further comprising:

means for determining the decreasing pressure $P_c$ associated with the peak negative derivative pressure $dP/dt_{NP}$ from the set of ventricular pressure values;

means for calculating an index $\beta$ of the slope of the early ejection pressure in the blood ejection phase in accordance with the formula $\beta=(P_c-P_b)/(t_c-t_b)$, wherein the severity of ventricular afterload is proportional to the magnitude of the index $\beta$; and means for adjusting one of a therapy delivery operating mode or parameter to minimize the magnitude of index $\beta$.

39. The apparatus of claim 37 wherein the obtaining means further comprises means for obtaining a set of right ventricular pressure values of right ventricular blood pressure within a right ventricle at sample times during the blood ejection phase of the right ventricle.

40. The apparatus of claim 37, wherein the obtaining means further comprises means for obtaining a set of left ventricular pressure values of left ventricular blood pressure within a left ventricle at sample times during the blood ejection phase of the left ventricle.

41. In an implantable medical device adapted to be implanted in a patient's body for delivering a therapy in accordance with adjustable therapy delivery operating modes and parameters comprising a pressure sensor coupled with pressure signal processing circuitry and therapy delivery means for delivering a therapy, apparatus that derives an index of ventricular afterload presenting resistance to ejection of blood from a ventricle during a blood ejection phase comprising:

means for obtaining a set of ventricular pressure values of blood pressure within a ventricle at sample times during the blood ejection phase of the ventricle;

means for determining the peak positive pressure value $P_b$, the peak negative derivative pressure $dP/dt_{NP}$, and the decreasing pressure $P_c$ associated with the peak negative derivative pressure $dP/dt_{NP}$ from the set of ventricular pressure values;

means for determining the sample time $t_b$ of peak positive pressure, and the sample time $t_c$ of the peak negative derivative pressure $dP/dt_{NP}$ from the sample times associated with the set of ventricular pressure values;

means for calculating an index $\beta$ of the slope of the early ejection pressure in the blood ejection phase in accordance with the formula $\beta=(P_c-P_b)/(t_c-t_b)$, wherein the severity of ventricular afterload is proportional to the magnitude of the index $\beta$; and means for adjusting one of a therapy delivery operating mode or parameter to minimize the magnitude of index $\beta$.

42. The apparatus of claim 41, wherein the obtaining means further comprises means for obtaining a set of right ventricular pressure values of right ventricular blood pressure within a right ventricle at sample times during the blood ejection phase of the right ventricle.

43. The apparatus of claim 41, wherein the obtaining means further comprises means for obtaining a set of left ventricular pressure values of left ventricular blood pressure within a left ventricle at sample times during the blood ejection phase of the left ventricle.

* * * * *

UNITED STATES PATENT AND TRADEMARK OFFICE
CERTIFICATE OF CORRECTION

PATENT NO. : 6,887,207 B2 Page 1 of 1
APPLICATION NO. : 10/376064
DATED : May 3, 2005
INVENTOR(S) : Douglas A. Hettrick It is certified that error appears in the above-identified patent and that said Letters Patent is hereby corrected as shown below:

Col. 15, line 3, delete "$\alpha = (t_b - t_a) / (t_{c-ta})$,"

and insert in place thereof -- $\alpha = (t_b - t_a) / (t_c - t_a)$, --

Claim 31, Col. 20, line 4, delete "is proportioned to"

and insert in place thereof -- is proportional to --

Signed and Sealed this

Tenth Day of March, 2009

JOHN DOLL
*Acting Director of the United States Patent and Trademark Office*